US010975333B2

(12) United States Patent
Larson

(10) Patent No.: US 10,975,333 B2
(45) Date of Patent: Apr. 13, 2021

(54) CONTROLLED RATE OF FOAM BREAKAGE IN HARD SURFACE CLEANERS

(71) Applicant: Ecolab USA, Inc., Saint Paul, MN (US)

(72) Inventor: Dale Larson, Eagan, MN (US)

(73) Assignee: ECOLAB USA INC., Saint Paul, MN (US)

( * ) Notice: Subject to any disclaimer, the term of this patent is extended or adjusted under 35 U.S.C. 154(b) by 0 days.

(21) Appl. No.: 15/189,225

(22) Filed: Jun. 22, 2016

(65) Prior Publication Data

US 2017/0015945 A1 Jan. 19, 2017

Related U.S. Application Data

(60) Provisional application No. 62/192,267, filed on Jul. 14, 2015.

(51) Int. Cl.

| | |
|---|---|
| ***C11D 1/62*** | (2006.01) |
| ***C11D 1/75*** | (2006.01) |
| ***C11D 1/835*** | (2006.01) |
| ***C11D 3/36*** | (2006.01) |
| ***C11D 3/00*** | (2006.01) |
| ***C11D 3/48*** | (2006.01) |

(Continued)

(52) U.S. Cl.

CPC .............. *C11D 3/0094* (2013.01); *C11D 1/62* (2013.01); *C11D 1/75* (2013.01); *C11D 3/2041* (2013.01); *C11D 3/2044* (2013.01); *C11D 3/2048* (2013.01); *C11D 3/2068* (2013.01); *C11D 3/30* (2013.01); *C11D 3/43* (2013.01); *C11D 3/48* (2013.01); *C11D 11/0023* (2013.01)

(58) Field of Classification Search

CPC ........... C11D 1/62; C11D 1/75; C11D 3/2068; C11D 3/2041; C11D 3/2044; C11D 3/30; B08B 3/08

USPC ....... 510/182, 191, 238, 433, 499, 504, 505, 510/506; 134/34, 40, 41

See application file for complete search history.

(56) References Cited

U.S. PATENT DOCUMENTS 4,065,409 A 12/1977 Flanagan
5,573,710 A 11/1996 McDonell (Continued)

FOREIGN PATENT DOCUMENTS

EP 0314232 A2 5/1989
EP 0691397 A2 1/1996

(Continued)

OTHER PUBLICATIONS

CCI—Cola Lipid Products, p. 1-12, 2004. (Year: 2004).*

(Continued)

*Primary Examiner* — Gregory R Delcotto
(74) *Attorney, Agent, or Firm* — McKee, Voorhees & Sease, PLC

(57) ABSTRACT

The present invention relates to mildly alkaline bathroom and/or hard surface cleaners providing improved foam performance. In particular, a concentrated, preferably disinfecting, high performance foaming cleaning composition is disclosed which can reduce or eliminate the need for scrubbing on bathroom and other hard surfaces. Methods of use are further disclosed for bathroom and/or other hard surface cleaning. The foam has increased stability for a period of time, followed by dissipation with an audible "crackling" sound and easy rinsability.

13 Claims, 1 Drawing Sheet

(51) Int. Cl.

| | |
|---|---|
| ***C11D 11/00*** | (2006.01) |
| ***C11D 3/20*** | (2006.01) |
| ***C11D 3/43*** | (2006.01) |
| ***C11D 3/30*** | (2006.01) |

(56) References Cited

U.S. PATENT DOCUMENTS

| | | | | |
|---|---|---|---|---|
| 5,948,741 | A | 9/1999 | Ochomogo et al. | |
| 6,090,771 | A | 7/2000 | Burt et al. | |
| 6,159,924 | A | 12/2000 | Weller et al. | |
| 6,165,965 | A * | 12/2000 | Schalitz | A01N 63/00 510/199 |
| 6,245,228 | B1 * | 6/2001 | Kelada | C02F 1/002 210/206 |
| 6,277,805 | B1 * | 8/2001 | Kupneski | C11D 1/62 510/384 |
| 6,514,923 | B1 * | 2/2003 | Cheung | C11D 1/004 510/191 |
| 6,693,070 | B1 * | 2/2004 | Cheung | A01N 33/12 510/235 |
| 8,563,490 | B2 * | 10/2013 | Cox | A61K 8/44 510/119 |
| 2001/0003738 | A1 | 6/2001 | Wise | |
| 2001/0049347 | A1 | 12/2001 | Robbins et al. | |
| 2002/0103098 | A1 * | 8/2002 | Harrison | C11D 1/86 510/382 |
| 2004/0224867 | A1 | 11/2004 | Colurciello et al. | |
| 2006/0009369 | A1 * | 1/2006 | Kilkenny | A01N 33/12 510/504 |
| 2006/0128585 | A1 * | 6/2006 | Adair | C11D 1/62 510/383 |
| 2008/0039352 | A1 * | 2/2008 | Wells | A61K 8/898 510/122 |
| 2008/0312327 | A1 * | 12/2008 | Rypkema | A61K 8/342 514/570 |
| 2009/0005281 | A1 * | 1/2009 | Hutton, III | A61K 8/41 510/125 |
| 2010/0160201 | A1 * | 6/2010 | Scheuing | C11D 1/83 510/180 |
| 2012/0213759 | A1 * | 8/2012 | Karsten | C11D 1/62 424/94.1 |
| 2013/0101677 | A1 * | 4/2013 | Callahan | A01N 33/12 424/616 |
| 2014/0011726 | A1 * | 1/2014 | Mitchell | C11D 3/48 510/391 |
| 2014/0116917 | A1 | 5/2014 | Scheuing et al. | |

FOREIGN PATENT DOCUMENTS

| | | | |
|---|---|---|---|
| JP | 2002146395 | A | 5/2002 |
| JP | 2012121959 | A | 6/2012 |
| JP | 2014237777 | A | 12/2014 |
| WO | 2002055650 | A1 | 7/2002 |
| WO | 2015091163 | A1 | 6/2015 |

OTHER PUBLICATIONS

CCI—Cola Lipid C, p. 1-4, Sep. 2014 (Year: 2014).*

Ecolab USA Inc., PCT/US2016/038599 filed Jun. 22, 2016, "The International Search Report and the Written Opinion of the International Searching Authority" dated Aug. 25, 2016, 15 pages.

* cited by examiner

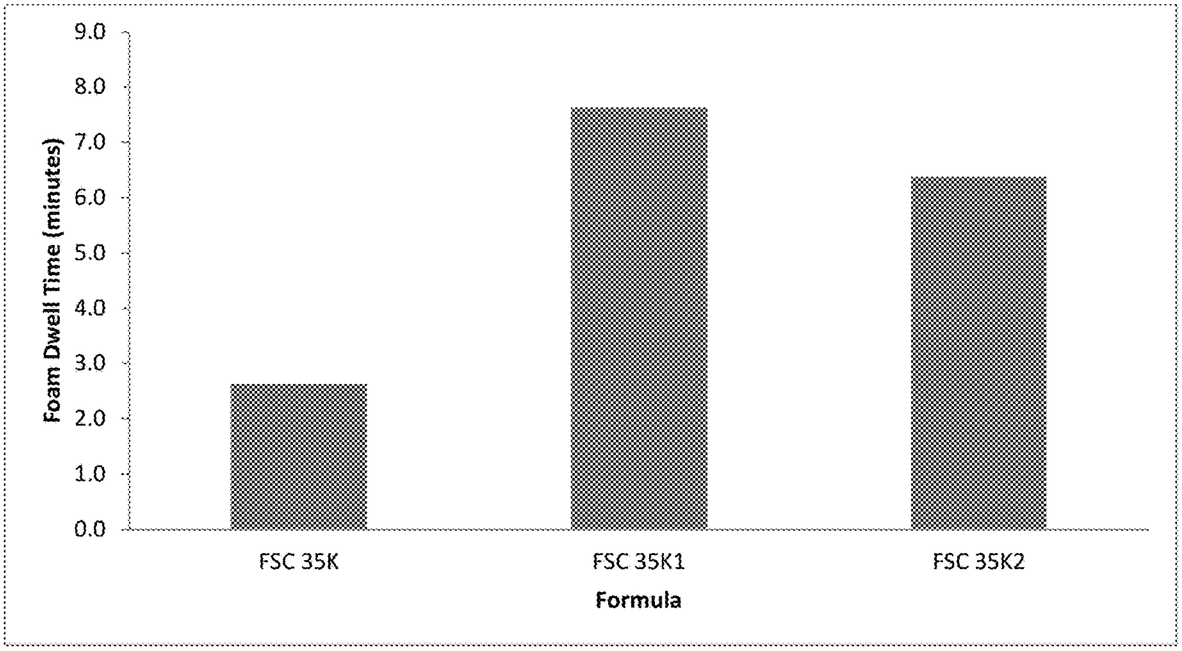
9.0
8.0
7.0
6.0
5.0
4.0
3.0
2.0
1.0
0.0
Foam Dwell Time (minutes)
FSC 35K
FSC 35K1
FSC 35K2
Formula

CONTROLLED RATE OF FOAM BREAKAGE IN HARD SURFACE CLEANERS

CROSS-REFERENCE TO RELATED APPLICATIONS

This application claims priority under 35 U.S.C. § 119 to provisional application Ser. No. 62/192,267, filed Jul. 14, 2015, herein incorporated by reference in its entirety.

FIELD OF THE INVENTION

The present invention relates to bathroom and/or hard surface cleaners providing improved foam performance. In particular, a concentrated, disinfecting, high performance foaming cleaning composition is disclosed which can reduce or eliminate the need for scrubbing on bathroom and other hard surfaces. Methods of use are further disclosed for bathroom and/or other hard surface cleaning.

BACKGROUND OF THE INVENTION

Many cleaning compositions include foaming agents and/or use a spray apparatus to deliver a foamed product. The foam increases contact time on surfaces to be cleaned, reduces scrubbing and also gives the appearance of increased cleaning abilities. Foamed compositions are used in many applications, including retail, industrial and institutional including grease cutters, clinging lime scale removers, shower wall cleaners, bathtub cleaners, hand sanitizing gels, disinfectant gels, hand-soaps, teat dips, coatings, stabilized enzymes, structured liquids, and the like.

Despite the use of foam, improvements are always desired to cleaning efficiency, so that multiple application cycles or scrubbing and/or high-pressure water-hosing, or longtime waiting, after the cleaning composition is applied on a stained surface, are normally not required. Thus foam must be stable and copious at first, then should dissipate for ease of rinsing and to reduce the wait time. Timing of foam development and dissipation are critical to cleaning compositions which cannot sacrifice cleaning ability.

The use of foam, however has presented further challenges. One problem that has been experienced in formulating foamable compositions is the ability to incorporate certain useful chemicals into the compositions. For example, many useful chemicals have characteristics that make their incorporation into foamable compositions somewhat problematic. For example, many cleaning solvents, such as solvents used to remove paint and/or grease, and many skin care agents, such as warming agents, reduce the surface tension of water and other liquids below that needed to maintain the integrity of the lamellae of a foam bubble. Such ingredients also displace surfactant molecules at the air/water interface disrupting the stability of any foam being formed and causing collapse. In addition, some of the above ingredients lose their effectiveness when combined with water, which has traditionally been used as a foam carrier in foamable compositions due to its polar nature.

The mechanisms for creating foam are also a challenge. There are a number of cleaning products on the market that foam as a result of a propellant. These types of products can be referred to as aerosols. Exemplary commercial aerosol products are available under the names Windex Powerized Foaming Glass & Multi-Surface Cleaner from S.C. Johnson, and Spray Cleaner from Ecolab Inc. An exemplary product that can be foamed using a mechanical foaming head is available under the name Scrubbing Bubbles from S.C.

Johnson. Exemplary patents and publications that describe compositions that can be foamed include U.S. Pat. No. 4,921,629 to Malihi et al.; U.S. Pat. No. 6,096,702 to Ramirez et al.; U.S. Pat. No. 5,866,524 to Wevers; and U.S. Patent Publication No. US2002/0072481 to Hubert et al. The use of aerosols make transportation difficult and expensive.

In view of the above, a need currently exists for control of foaming in cleaning compositions to produce consistent cleaning ability, stable foam on delivery and dissipation for certain cleaning operations, while other operations may require a longer foam time.

It is an object of the present invention to develop foamable cleaning compositions that satisfy the above needs as well as other objectives of the invention that will become apparent from the description of the invention which follows.

BRIEF SUMMARY OF THE INVENTION

The present invention provides moderately alkaline bathroom and/or hard surface cleaners providing highly effective soil removal capabilities and improved foam characteristics. In particular, the compositions provide significant cleaning benefits to reduce or eliminate the need for scrubbing by foam stability for a period of time, followed by dissipation with an audible "crackling" sound and easy rinsability.

In one embodiment, the present invention is a cleaning composition comprising a specific combination of a foaming surfactant, a foaming synergist (typically a solvent), and a foam antagonist. The invention includes from about 0.5 wt-% to about 20 wt-% of a foaming surfactant, preferably amphoteric (amine oxide), from about 0.5 wt-% to about 15 wt-% of foaming synergist (solvent); and from about 0.5 wt-% to about 15 wt-% of foaming antagonist (polymer or lightly water insoluble quat), with the remainder being water. The composition can further comprise from about 0.5 wt-% to about 40 wt-% of a chelant, as well as a further components including a pH adjusting agent, a biocide or antimicrobial agent, and other ingredients such as dyes and fragrances and the like.

In a still further embodiment, the present invention is a method for cleaning bathroom surfaces and/or other hard surfaces comprising: contacting a soiled surface for a period of time sufficient to remove dirt, debris, soap scum, hard water stains and the like, with a foaming aqueous composition comprising from about 0.5 wt-% to about 20 wt-% of a foaming surfactant, preferably amphoteric (amine oxide), from about 0.5 wt-% to about 15 wt-% of foaming synergist (solvent); and from about 0.5 wt-% to about 15 wt-% of foaming antagonist (polymer or slightly water insoluble quat), with the remainder being water at approximately form about 50-80 wt-%; and after allowing said foam to dissipate or "crackle", rinsing said surface to removing said soils and any remaining cleaning composition from said surface.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

FIG. 1 shows a graph soil foam dwell time on a slanted surface with formulations according to the invention, FSC 35K and FSC 35K1; and a typical foaming bathroom cleaning composition.

DETAILED DESCRIPTION OF THE INVENTION

The embodiments of this invention are not limited to particular bathroom and/or hard surface cleaning compositions and methods of using the same, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism. For the purpose of this patent application, successful microbial reduction is achieved when the microbial populations are reduced by at least about 50%, or by significantly more than is achieved by a wash with water. Larger reductions in microbial population provide greater levels of protection.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces.

The term "substantially similar cleaning performance" refers generally to achievement by a substitute cleaning product or substitute cleaning system of generally the same degree (or at least not a significantly lesser degree) of cleanliness or with generally the same expenditure (or at least not a significantly lesser expenditure) of effort, or both. As used herein, the term "cleaning performance" may be measured in terms of percentage of soil removal.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

The cleaning composition can be referred to as a cleaning composition and can be provided in the form of a concentrated cleaning composition, a ready-to-use detergent composition, and/or a use composition. The phrase "cleaning composition" refers to a composition that provides for the removal of a substance from a surface to be cleaned. Exemplary substances that can be removed by the cleaning composition include soil, dirt, oil, grease, bacteria, microbes, viruses, etc.

The concentrated cleaning composition can be referred to as the concentrate, and can be diluted to provide the ready-to-use cleaning composition and/or the cleaning use composition. The concentrate can be diluted in a single dilution or in stages to provide the ready-to-use cleaning composition and/or the cleaning use composition. Providing the cleaning composition as a concentrate for subsequent dilution can be advantageous when it is desirable to package and ship the concentrate instead of the ready-to-use cleaning composition and/or the cleaning use composition. The ready-to-use cleaning composition can be made available as a use composition when the ready-to-use cleaning composition is intended to be applied directly to a surface to provide cleaning. For example, a glass cleaner can be referred to as a ready-to-use composition when it is intended to be applied directly to a glass surface for cleaning.

The cleaning composition according to the invention is preferably foamed and applied to a surface. In general, it is expected that the cleaning composition will provide cleaning in environments where application of a foam to a surface is advantageous. An exemplary environment where application of a foam to a surface is advantageous is where the foam provides for increasing contact time between the cleaning composition and the surface to be cleaned. By providing the cleaning composition in the form of a foam, the tendency of the cleaning composition to run or level when applied to a surface can be reduced. When cleaning a non-horizontal surface (such as a vertical surface), providing the cleaning composition in the form of a foam can enhance cling that allows the foam cleaning composition to remain in place and resist running off or down the non-horizontal surface as a result of gravity. Exemplary non-horizontal surfaces that are often cleaned include walls, doors, windows, and mirrors. In the case of horizontal surfaces, the foam cleaning composition can resist leveling. This is advantageous in a situation, such as, cleaning a floor where it is desirable to have the foam cleaning composition remain in a specific location on the floor without running across the floor and/or running under a door. When the cleaning composition is provided as a foam, the composition has a cellular structure that can be characterized as having several layers of air cells that provide the composition with a foamy appearance. It should be understood that the characterization of a foam refers to the existence of more than simply a few air bubbles. In general, a foam can be characterized as having at least 50 wt. % foam using a 15 second vertical separation test.

The test is carried out by spraying the cleaning composition as a foam onto a vertical surface such as glass, waiting 15 seconds after application of the foam to the vertical surface, and then taking up the liquid portion and the foam portion in separate preweighted paper towels. The weight of the absorbed liquid can be calculated and the weight of the absorbed foam can be calculated. By providing a separation time of at least 15 seconds, it is believed that a reasonable amount of separation of liquid and foam can be achieved. The towel picking up the liquid portion should not pick up any of the foam portion, and the towel picking up the foam portion should not pick up the liquid portion that has fallen below the foam portion. It is understood that the foam portion may still include a small amount of associated liquid. However, this associated liquid is considered a part of the foam as long as it remains with the foam at the 15 second cut off time. The weight percent foam can be calculated by dividing the weight of the foam component by the total weight and multiplying by 100. The 15 second vertical separation test can be referred to as a "gravimetric foam test after 15 seconds."

The cleaning composition preferably provides at least 70 wt. % foam according to the gravimetric foam test after 15 seconds, more preferably at least about 90 wt. % foam, and even more preferably at least about 95 wt. % foam. In general, it is desirable to have the foam hang up and not fall down a vertical surface to provide desired contact time and to allow a person sufficient time to work the foam at its intended location. The period of 15 seconds is selected for the test because it is expected that a foam will likely "hang" for at least about 15 seconds and any free liquid, if present at all, will have an opportunity to separate from the foam and fall down the vertical surface. In addition, the foam persists for at least about 15 seconds after application to a surface. This means that the foam will have a tendency to remain as a foam and will resist condensing to a liquid in order to provide the above-identified weight percent foam. More preferably, the foam persists for at least about 1 minute after application to the surface.

The cleaning composition can be formulated for various types of cleaning applications where delivery as a foam is advantageous. Exemplary applications where delivery as a foam is advantageous include hard surface cleaning compositions, hard surface antimicrobial compositions, toilet bowl cleaning compositions, carpet cleaning composition, glass cleaning composition, skin care products, floor strippers, floor finishes, presoaks, detergents, wheel cleaners, tire dressings, polishes, and pesticides. When used as an antimicrobial formulation, the composition can be used on hard surfaces, meats, vegetables, fabrics, and skin. When used as a hard surface cleaner, the composition can be applied to stainless steel, aluminum, copper, vinyl, plastic, metal, glass, rubber (natural and synthetic), formica, wood, mild steel, melamine, brass, ceramic, stone, etc. In addition, the composition can be advantageously used on nonhorizontal surfaces including those surfaces found on toilets, glass, mirrors, showers, transportation vehicles, walls, etc.

Exemplary fabrics on which the composition can be used includes wovens, nonwovens, knits, etc., and can be used as a prespotter for laundry and carpets. Exemplary skin care products that can be provided include soaps, lotions, etc. Exemplary carpet/textile cleaners that can be provided include spotters, bleaches, rust removers, softeners, and detergents. When provided as a floor stripper, the composition can maintain its position on the floor rather than leveling and, for example, running under a door. When the composition is provided as a polish, it can be applied to appliances and other devices such as refrigerators, stoves, dishwashers, elevators, doors, faucets, countertops, sinks, etc. When provided as a pesticide, the composition can be foamed to fill difficult to access areas and non-horizontal surfaces.

The composition according to the invention can be foamed without the use of a propellant, and applied as a foam directly to a surface. A solvent can assist in the generation of a foam when the composition is processed through a mechanical foaming head. The solvents that assist in the generation of a foam can be referred to as "foam-boosting solvents." Mechanical foaming heads that can be used according to the invention to provide foam generation include those heads that cause air and the cleaning composition to mix and create a foamed composition. That is, the mechanical foaming head causes air and the cleaning composition to mix in a mixing chamber and then pass through an opening to create a foam.

The cleaning composition according to the invention can be foamed without the use of a propellant normally and is preferably foamed through pump up foamers by mechanical means rather than pressure or aerosol, although these may be used. In general, aerosol compositions include a pressurized container for storing a composition and a propellant. The expansion of the propellant in the composition and propellant mixture as it passes through a nozzle causes the cleaning composition to become foamed. The mechanical foaming head utilized according to the invention, in contrast, relies upon air from the environment and causes the air to mix with the liquid composition to become foamed.

Propellants that are often used in aerosols include liquids that form gases when expanded to atmospheric pressure. Exemplary propellants commonly used in aerosols include fluorocarbons, chlorofluorocarbons, and alkanes such as butane, ethane, isobutane, and propane. Propellants in general and these propellants in particular can be excluded from the cleaning composition according to the invention or they can be limited to an amount, if any are present, that is insufficient to provide foaming of the composition as a result of pressure drop (such as through an aerosol nozzle) so that the composition contains at least 50 wt. % foam according to a 15 second vertical separation test. Air has a tendency not to compress to a liquid under conditions normally encountered in conventional aerosol devices. Air is not considered a propellant according to the present invention even though it may be slightly compressed using the mechanical foaming head according to the invention. The term "propellant" as used herein should be understood to not refer to air and can be characterized as non-air containing propellants. The foam according to the invention can be characterized as having been formed by air rather than by a propellant. Because propellants are typically provided in a liquid form in combination with a liquid to be foamed, and form bubbles in the liquid as the propellant vaporizes as pressure drops, it is expected that the foam that is foamed by a propellant will contain residual propellant. It is believed that the residual propellant can be measured by a gas chromatographic head space analysis. It is expected that foams produced using a propellant will exhibit a concentration of propellant in the foam of greater than 1 ppm. Accordingly, the foam according to the invention includes less than 1 ppm propellant as measured by a gas chromatographic head space analysis. Preferably, the foam according to the invention has no propellant. That is, the foam according to the invention can be produced using air and need not be produced using a propellant.

Because the foam according to the invention can be prepared without a propellant, the container that holds the liquid cleaning composition can be constructed so that that it is capable of holding the cleaning composition under substantially atmospheric conditions both inside and outside the container. Because propellants are preferably not used, the container need not be a container capable of withstanding the pressures normally associated with aerosol containers. Accordingly, the container can be provided from a plastic or polymer material rather than from a metallic material normally associated with aerosol containers.

Exemplary mechanical foaming heads that can be used according to the invention include those available from Airspray International, Inc. of Pompano Beach, Fla., and from Zeller Plastik, a division of Crown Cork and Seal Co. Exemplary mechanical foaming heads that can be used according to the invention are described in, for example, U.S. Pat. No. D-452,822; U.S. Pat. No. D-452,653; U.S. Pat. No. D-456,260; and U.S. Pat. No. 6,053,364. Mechanical foaming heads that can be used according to the invention includes those heads that are actuated or intended to be actuated by application of finger pressure to a trigger that causes the cleaning composition and air to mix and create a foam. That is, a person's finger pressure can cause the trigger to depress thereby drawing the cleaning composition and air into the head and causing the cleaning composition and air to mix and create a foam.

Cleaning Compositions

The present invention provides moderately alkaline bathroom and/or hard surface cleaning compositions with improved foaming and which provide highly effective soil removal capabilities. In particular, the compositions provide significant cleaning benefits to reduce or eliminate the need for scrubbing by foam stability for a period of time, followed by dissipation with an audible "crackling" sound and easy risibility.

The present invention includes a combination of a foaming surfactant, a foaming synergist, and a foam antagonist. The foaming surfactant needs to be present in the concentrate in an amount of at least 4 wt-%, and the foaming antagonist needs to be present in an amount of at least 2 wt-%.

In one embodiment, the present invention is a cleaning composition comprising a specific combination of a foaming surfactant, a foaming synergist (typically a solvent), and a foam antagonist. The invention includes from about 0.5 wt-% to about 20 wt-% of a foaming surfactant, preferably amphoteric (amine oxide), from about 0.5 wt-% to about 15 wt-% of foaming synergist (solvent); and from about 0.5 wt-% to about 15 wt-% of foaming antagonist (polymer or lightly water insoluble quat), with the remainder being water. The composition can further comprise from about 0.5 wt-% to about 40 wt-% of a chelant, as well as a further components including a pH adjusting agent, a biocide or antimicrobial agent, and other ingredients such as dyes and fragrances and the like.

In a further embodiment the invention includes an amine oxide foaming surfactant, preferably one of more of lauryl dimethyl amine oxide, cocamine oxide, and/or octyl dimethyl amine oxide, a foaming synergist of diethylene glycol butyl ether, and/or cocamidopropyl phosphatidyl PG-dimonium chloride, and a foaming antagonist of a quaternary ammonium compound. The invention can further preferably include a chelant, and a pH adjusting agent.

In a still further embodiment, the present invention is a method for cleaning bathroom surfaces and/or other hard surfaces comprising: contacting a soiled surface for a period of time sufficient to remove dirt, debris, soap scum, hard water stains and the like, with a foaming aqueous composition comprising from about 0.5 wt-% to about 20 wt-% of a foaming surfactant, preferably amphoteric (amine oxide), from about 0.5 wt-% to about 15 wt-% of foaming synergist (solvent); and from about 0.5 wt-% to about 15 wt-% of foaming antagonist (polymer or lightly water insoluble quat), with the remainder being water 50-80%; and after allowing said foam to dissipate, rinsing said surface to remove said soils and any remaining cleaning composition from said surface.

The concentrated compositions and/or use dilutions of the concentrated compositions, and/or ready-to-use dilute concentration compositions according to the invention provide significant utility for use as both bathroom cleaners and hard surface cleaners. The liquid or aqueous compositions disclosed according to the invention are particularly suitable for use as a dilutable cleaning concentrate or as a ready-to-use product. According to the invention, a concentrate refers to a composition that is intended to be further diluted with water to provide a use solution. A use solution refers to an aqueous composition that can be applied directly to surfaces. In general, a use solution can have a solids content of less than about 90 wt-%, whereas the solids content refers to the weight percent of non-water components.

The compositions are dissolved in water to form a stable solution. Additional stabilizing agents may be employed to improve phase stability of the compositions as disclosed herein. The compositions according to the invention may be provided in various forms for providing cleaning compositions for use according to the methods of the invention. According the invention, the compositions are provided as a liquid. The compositions may be dispensed from single or multi-use packaging in the concentrated and/or ready-to-use product formulations.

Foaming Surfactant

According to the invention the cleaning compositions include at least one foaming surfactant. Preferably the foaming surfactant is an amphoteric and/or nonionic surfactant such as an amine oxide surfactant. The amphoteric surfactant should have good foam stability, generally good soil penetration and should be easily rinsed.

Suitable amphoteric surfactants include water-soluble betaine and propionate surfactants or mixtures thereof. Betaine surfactants are suitably chosen from those of the general formula

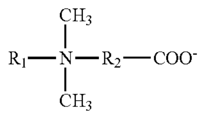

wherein $R_1$ is an alkyl group containing from 8 to 18 carbon atoms, or the amido radical which may be represented by the following general formula:

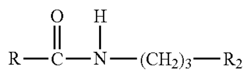

wherein R is an alkyl group having from 8 to 18 carbon atoms, a is an integer having a value of from 1 to 4 inclusive, and $R_2$ is a $C_1$-$C_4$ alkylene group. Examples of such water-soluble betaine surfactants include dodecyl dimethyl betaine, as well as cocoamidopropylbetaine, (e.g. Lakeland CAB and Surfac B4), cocoalkyl dimethyl betaine (e.g. Lakeland CTA/N) and bis-(1,2-ethanediol) tallow dimethyl betaine (e.g. Lakeland TAB II).

Suitable propionate surfactants include dipropionates or monopropionates of the formula

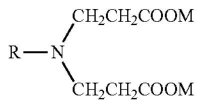

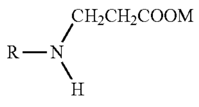

wherein R is a $C_{8-22}$ alkyl group, and M is hydrogen or an alkali metal ion, for example sodium or potassium.

Examples of such water-soluble propionate surfactants include dipropionates such as β-alanine, N-(2-carboxy ethyl) N-coco alkyl derivatives (e.g. Lakeland AMA, AMA 38 or AMA 100), N-(2-carboxyethyl) N-tallow alkyl derivative (30% solution) (e.g. Lakeland ODA), cocamidopropionate sodium salts (e.g. Librateric AA-30 and AA-38) and monopropionates such as N-cocoalkylaminopropionic acid (e.g. Lakeland ACP 70) or mixtures thereof.

Further suitable amphoteric surfactants include alkylamine dicarboxylates such as Surfac BH30, β-alanine, N-(2-carboxy ethyl) N-coco alkyl derivatives and sodium salts thereof, cocamidopropylbetaine, alkylamine dicarboxylates and mixtures thereof.

Nonionic surfactants useful in the present invention generally have good water solubility, high foaming properties, good grease solubilising properties and are easily rinsed.

Other foaming surfactants can include suitable nonionic surfactants such as semi-Polar Nonionic Surfactants. Generally, semi-polar nonionics are high foamers and foam stabilizers, which can limit their application in CIP systems. However, within compositional embodiments of this invention designed for high foam cleaning methodology, semi-polar nonionics would have immediate utility. The semi-polar nonionic surfactants include the amine oxides, phosphine oxides, sulfoxides and their alkoxylated derivatives.

Amine oxides are tertiary amine oxides corresponding to the general formula:

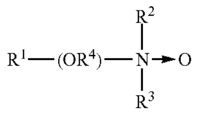

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkaline or a hydroxyalkylene group containing 2 to 3 carbon atoms; and n ranges from 0 to about 20.

Useful water soluble amine oxide surfactants are selected from the coconut or tallow alkyl di-(lower alkyl) amine oxides, specific examples of which are dodecyldimethylamine oxide, tridecyldimethylamine oxide, etradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Useful semi-polar nonionic surfactants also include the water soluble phosphine oxides having the following structure:

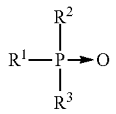

wherein the arrow is a conventional representation of a semi-polar bond; and, le is an alkyl, alkenyl or hydroxyalkyl moiety ranging from 10 to about 24 carbon atoms in chain length; and, $R^2$ and $R^3$ are each alkyl moieties separately selected from alkyl or hydroxyalkyl groups containing 1 to 3 carbon atoms.

Examples of useful phosphine oxides include dimethyldecylphosphine oxide, dimethyltetradecylphosphine oxide, methylethyltetradecylphosphone oxide, dimethylhexadecylphosphine oxide, diethyl-2-hydroxyoctyldecylphosphine oxide, bis(2-hydroxyethyl)dodecylphosphine oxide, and bis(hydroxymethyl)tetradecylphosphine oxide.

Semi-polar nonionic surfactants useful herein also include the water soluble sulfoxide compounds which have the structure:

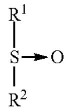

wherein the arrow is a conventional representation of a semi-polar bond; and, $R^1$ is an alkyl or hydroxyalkyl moiety of about 8 to about 28 carbon atoms, from 0 to about 5 ether linkages and from 0 to about 2 hydroxyl substituents; and $R^2$ is an alkyl moiety consisting of alkyl and hydroxyalkyl groups having 1 to 3 carbon atoms.

Useful examples of these sulfoxides include dodecyl methyl sulfoxide; 3-hydroxy tridecyl methyl sulfoxide; 3-methoxy tridecyl methyl sulfoxide; and 3-hydroxy-4-dodecoxybutyl methyl sulfoxide.

Semi-polar nonionic surfactants for the compositions of the invention include dimethyl amine oxides, such as lauryl dimethyl amine oxide, myristyl dimethyl amine oxide, cetyl dimethyl amine oxide, combinations thereof, and the like. Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-$(EO)_5(PO)_4$) and Dehypon LS-36 (R-$(EO)_3(PO)_6$); and capped alcohol alkoxylates, such as Plurafac LF221 and Tegoten EC11; mixtures thereof, or the like.

Other examples include polyethylene oxide condensates of alkyl phenols, such as the condensation products of $C_{6-12}$ alkyl phenols with 5 to 25 moles of ethylene oxide per mole of alkyl phenol. Examples include nonyl phenol condensed with about 9.5 moles of ethylene oxide per mole of nonyl phenol; dodecylphenol condensed with about 12 moles of ethylene oxide per mole of phenol; dinonyl phenol condensed with about 15 moles of ethylene oxide per mole of phenol and diisooctyl phenol condensed with about 15 moles of ethylene oxide per mole of phenol.

Further useful nonionic surfactants include condensation products of $C_8$-$_{22}$ aliphatic alcohols with from about 1 to about 60 moles of ethylene oxide. Examples include the condensation product of myristyl alcohol with about 10 moles of ethylene oxide per mole of alcohol, the condensation product of coconut alcohol (C10-14) with about 9 moles of ethylene oxide, the condensation product of $C_6$-$C_{11}$ straight-chain alcohols with from about 3 to about 6 moles of ethylene oxide, e.g. Alfonic®810-4.5 (HLB of about 12), Alfonic®810-2 (HLB of about 12); and Alfonic® 610-3.5 (HLB of 10), or polyoxyethylene (6) C9-11 alcohol, eg Surfac UN 65/95, Neodol 91-6 and Caflon NE600.

Further examples of useful nonionic surfactants include the Neodol $C_{9.\ 11}$ ethoxylated alcohols available from Shell Chemical Company, e.g. Neodol 91-2.5 (having about 2.5 ethoxy groups per molecule), Neodol 91-6 (having about 6 ethoxy groups per molecule) and Neodol 91-8 (having about 8 ethoxy groups per molecule). Still further examples of ethoxylated alcohols include the Rhodasurf® DA series of branched isodecyl alcohol ethoxylates available from Rhodia, e.g. Rhodasurf DA-530 (4 moles of ethoxylation and an HLB of 10.5), Rhodasurf DA-630 (6 moles of ethoxylation with an HLB of 12.5) and Rhodasurf DA-639 (a 90% solution of DA-630); and $C_{12-15}$ ethoxylated alcohols such as Neodol 25-12.

Other examples of useful nonionic surfactants include those having a formula $RO(CH_2CH_2O)_nH$ wherein R is a mixture of linear, even carbon-number hydrocarbon chains ranging from $C_{12}H_{25}$ to $C_{16}H_{33}$ and n represents the number of repeating units and is a number of from about 1 to about 12, for example, the Genapol 26-L series.

A further class of suitable nonionic surfactants include those based on alkoxy block copolymers, and in particular, compounds based on ethoxy/propoxy block copolymers. Polymeric alkylene oxide block copolymers include nonionic surfactants in which the major portion of the molecule is made up of block polymeric $C_2$-$C_4$ alkylene oxides. Such nonionic surfactants, while preferably built up from an alkylene oxide chain starting group, can have as a starting nucleus almost any active hydrogen containing group including, without limitation amides, phenols, thiols and secondary alcohols. Examples include those of the formula:

$$HO\text{-}(EO)_x(PO)_y(EO)_z\text{—}H$$

where EO represents ethylene oxide,

PO represents propylene oxide, y equals at least 15, $(EO)_{x+y}$ equals 20 to 50% of the total weight of said compounds, and, the total molecular weight is preferably in the range of about 2000 to 15,000, for example those available under the PLURONIC tradename from BASF or Emulgen from Kao.

Further suitable nonionic surfactants include those of the formula:

$R\text{-}(EO,PO)_a(EO,PO)_b\text{—}H$ wherein R is an alkyl, aryl or aralkyl group, where the R group contains 1 to 20 carbon atoms, the weight percent of EO is within the range of 0 to 45% in one of the blocks a, b and within the range of 60 to 10% in the other of the blocks a, b and the total number of moles of combined EO and PO is in the range of 6 to 125 moles, with 1 to 50 moles, with 1 to 50 moles in the PO rich block and 5 to 100 moles in the EO rich block.

These surfactants include butoxy derivatives of propylene oxide/ethylene oxide block polymers having molecular weights within the range of about 2000 to 5000.

Still further useful nonionic surfactants containing polymeric butoxy (BO) groups include those of the formula:

$RO\text{—}(BO)_n(EO)_x\text{—}H$ wherein R is an alkyl group containing 1 to 20 carbon atoms, n is about 5-15 and x is about 5-15.

Also useful are nonionic block copolymer surfactants, which also include polymeric butoxy groups, such as those of the formula:

$HO\text{-}(EO)_x(BO)_x(EO)_y\text{—}H$ wherein n is about 5-15, preferably about 15,
x is about 5-15, preferably about 15, and
y is about 5-15, preferably about 15.

Still further useful nonionic block copolymer surfactants include ethoxylated derivatives of propoxylated ethylene diamine, which may be represented by such those of the formula:

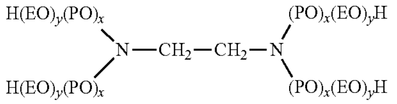

where (EO) represents ethoxy,
(PO) represents prepoxy, and
the amount of $(PO)_x$ is such as to provide a molecular weight prior to ethoxylation of about 300 to 7500, and the amount of $(EO)_y$ is such as to provide about 20% to 90% of the total weight of said compound.

Further suitable nonionic surfactants include amine oxides such as $C_{10-20}$ alkyl di($C_1$-$C_7$) amine oxides, e.g. lauryl dimethyl amine oxide, myristyl dimethyl amine oxide, dimethyl cocoamine oxide, dimethyl (hydrogenated tallow) amine oxide, and myristyl/palmityl dimethyl amine oxide; $C_{10-20}$ alkyl di(hydroxy $C_1$-$C_7$) amine oxides e.g. bis(2-hydroxyethyl) cocoamine oxide, bis(2-hydroxyethyl) tallowamide oxide, and bis(2-hydroxyethyl) stearylamineoxide;

$C_{10-20}$ alkylamidopropyl di($C_1$-$C_7$) amine oxides e.g. cocoamidoproyl dimethyl amine oxide and tallowamidopropyl dimethyl amine oxide; and $C_{10-20}$ alkymorpholine oxides.

Preferably the amine oxide constituent is an alkyl di(lower alkyl) amine oxide of the following structure:

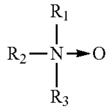

wherein each:
$R_1$ is a straight chained $C_1$-$C_4$ alkyl group, preferably both $R_1$ are methyl groups; and
$R_2$ is a straight chained $C_8$-$C_{18}$ alkyl group, preferably is $C_{10}$-$C_{14}$ alkyl group, most preferably is a $C_{12}$ alkyl group.
The amine oxide constituent is preferably lauryl dimethyl amine oxide.

Particularly useful amine oxides include for example amine oxides available in the AO series from Tomah Products Inc.; in the AMMONYX series from Stepan Co.; in the BARLOX series from Lonza Inc. (Fairlawn, N.J.), in the RHODAMOX series from Rhone-Poulenc Inc. (Cranbury N.J.), as well as in the MACKAMINE series of products from McIntyre Group Ltd, e.g. Mackamine CAO.

Further suitable nonionic surfactants include polyglucosides, including alkylmonoglucosides and alkylpolyglucosides. The alkylpolyglucosides are generally condensation products of long chain alcohols (e.g. $C_{8-30}$) with sugars, starches or polymers thereof. These compounds may have the formula $(S)_n\text{—}O\text{—}R$, where S is a sugar moiety such as glucose, fructose, mannose or galactose, n is an integer of from about 1 to about 1000, and R is a $C_{8-30}$ alkyl group. Suitable examples include Glucopon 625 CS and Glucopon 600CS.

Particularly preferred non-ionic surfactants for use in the present invention include polyoxyethylene (6), $C_{9-11}$ alcohols, $C_{9-15}$ ethoxylated alcohols, alkylpolyglucosides, amine oxides and mixtures thereof.

The one or more foaming surfactant is present in the composition in an amount of from about 0.5 wt-% to about 20 wt-%, preferably from about 1 wt-% to about 15 wt-% and more preferably from about 2 wt-% to about 12 wt-%.

Foaming Syngergist (Solvent)

The cleaning composition of the invention also includes at least one foaming synergist. This material is typically a solvent, or polymer such as a naturally derived phospholipid. The solvent used in the present invention is typically an organic solvent having a boiling point of from 70 to 180° C., preferably from 100° to 130° C. The solvent is preferably water-miscible. Suitable solvents are low-odor and non-tainting. Examples of suitable solvents include glycol ethers, such as those having the formula:

$R_a\text{—}O\text{—}R_b\text{—}OH$ wherein $R_a$ is an alkyl of 1 to 20 carbon atoms, or an aryl of at least 6 carbon atoms and $R_b$ is an alkylene of 1 to 8 carbons or is an ether or polyether containing from 2 to 20 carbon atoms.

Examples of suitable glycol ether solvents include ethylene glycol monobutyl ether (butyl cellosolve), diethylene glycol monobutyl ether (butyl carbitol), triethylene glycol monobutyl ether, mono-, di-, tri-propylene glycol monobutyl ether, tetraethylene glycol monobutyl ether, mono-, di-, tri-propylene glycol monomethyl ether, propylene glycol monomethyl, ether, ethylene glycol monohexyl ether, diethylene glycol monohexyl ether, propylene glycol tertiary butyl ether, ethylene glycol monoethyl ether, ethylene glycol monomethyl ether, ethylene glycol monopropyl ether, ethylene glycol monopentyl ether, diethylene glycol monomethyl ether, diethylene glycol monoethyl ether, diethylene glycol monopropyl ether, diethylene glycol monopentyl ether, triethylene glycol monomethyl ether, triethylene glycol monoethyl ether, triethylene glycol monopropyl ether, triethylene glycol monopentyl ether, triethylene glycol monohexyl ether, mono-, di-, tri-propylene glycol monoethyl ether, mono-, di-,tri-propylene glycol monopropyl ether, mono-, di-, tri-propylene glycol monopentyl ether, mono-, di-, tri-propylene glycol monohexyl ether, mono-, di-, tri-butylene glycol mono methyl ether, mono-, di-, tri-butylene glycol monoethyl ether, mono-, di-, tri-butylene glycol monopropyl ether, mono-, di-, tri-butylene glycol monobutyl ether, mono-, di-, tri-butylene glycol monopentyl ether, mono-, di-, tri-butylene glycol monohexyl ether, ethylene glycol monoacetate and dipropylene glycol propionate and mixtures thereof. Preferred examples include 1-methoxy-2-propanol (e.g. Dowanol PM) and 3-butoxy-propan-2-ol (e.g. Dowanol PnB).

Other suitable solvents include water-miscible alcohols, especially C1-4 alcohols, optionally substituted with a C1-4 alkoxy group, such as ethanol, propanol, butanol, isopropanol, and mixtures thereof.

Other suitable solvents include glycols, (such as ethylene glycol, propylene glycol and hexylene glycol), water-miscible ethers (such as diethylene glycol diethylether, and propylene glycol dimethylether), lower esters of monoalkyl ethers of ethylene glycol or propylene glycol (such as propylene glycol monomethyl ether acetate) and mixtures thereof.

Another class of foaming synergist includes Cola® Lipid C, chemically described as Cocamidopropyl Phosphatidyl PG-Dimonium Chloride, is a coconut oil derived phospholipid composed predominantly of diester and triester phosphatides with multiple chain groups. In addition to topically simulating the properties displayed by the polar stratum corneum lipids, Cola® Lipid C displays a broad range of functional attributes including gentle cleansing and foaming properties, anti-irritation effects when combined with anionic surfactants, unusually high substantivity, long lasting skin conditioning, and broad spectrum antimicrobial activity. Due to the ampholytic character of Cola® Lipid C, it is compatible with practically all other types of ingredients including anionic surfactants. Because Cola® Lipid C possesses this unique combination of properties and is virtually non-irritating to skin and eyes, it is an ideal ingredient for baby care products, sensitive skin cleansers and other personal care and health care products.

In an aspect, the compositions include from about 0.01 wt-%-15 wt-% solvent preferably from about 0.1 wt-%-12 wt-% and more preferably from about 0.5 wt-%-10 wt-%. In addition, without being limited according to the invention, all ranges recited are inclusive of the numbers defining the range and include each integer within the defined range.

Foaming Antagonist

The invention also includes a foaming antagonist, which is typically a slightly water insoluble quaternary ammonium compound. The antagonist in a preferred embodiment imparts antimicrobial activity such as for example a cationic active/cationic biocide.

The cationic or cationically-active ingredients are substances based on nitrogen centered cationic moieties with net positive change. The cationic or cationically-active ingredients are preferably selected from the group consisting of cationic polymers, cationic surfactants, cationic monomers, and betaine with at least one cationic or cationically-active group.

Suitable cationic active ingredients contain quaternary ammonium groups. Suitable cationic active ingredients especially include those of the general formula:

$$N^{(+)}R^1R^2R^3R^4X^{(-)}$$

wherein $R^1$, $R^2$, $R^3$ and $R^4$ independently of each other represent alkyl groups, aliphatic groups, aromatic groups, alkoxy groups, polyoxyalkylene groups, alkylamido groups, hydroxyalkyl groups, aryl groups, $H^+$ ions, each with from 1 to 22 carbon atoms, with the provision that at least one of the groups $R^1$, $R^2$, $R^3$ and $R^4$ has at least eight carbon atoms and wherein X(−) represents an anion, for example, a halogen, acetate, phosphate, nitrate or alkyl sulfate, preferably a chloride. The aliphatic groups can also contain cross-linking or other groups, for example additional amino groups, in addition to the carbon and hydrogen atoms.

Particular cationic active ingredients include, for example, but are not limited to, alkyl dimethyl benzyl ammonium chloride (ADBAC), alkyl dimethyl ethylbenzyl ammonium chloride, dialkyl dimethyl ammonium chloride, benzethonium chloride, N,N-bis-(3-aminopropyl) dodecylamine, chlorhexidine gluconate, an organic and/or organic salt of chlorhexidene gluconate, PHMB (polyhexamethylene biguanide), salt of a biguanide, a substituted biguanide derivative, an organic salt of a quaternary ammonium containing compound or an inorganic salt of a quaternary ammonium containing compound or mixtures thereof.

The cationic active will be compatible with the amphoteric and nonionic surfactants. Further, the antimicrobial optionally used in the invention must be suitably non-toxic and must be suitable for use in a kitchen environment. In particular, the biocide should be suitable for use according to The Biocidal Products Directive (BPD) 98/8/EC (HSE, UK) for use in product types 2 (Private and public health area disinfectants and other biocidal products) and 4 (Food and feed area disinfectants).

Additional suitable examples of cationic biocides to be included in the present invention include those of the general formula

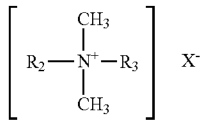

wherein $R_2$ and $R_3$ are the same or different $C_{8-12}$ alkyl, or $R_2$ is $C_{12-16}$ alkyl, $C_{8-18}$ alkoxyphenolethoxy and $R_3$ is benzyl, and X is a halide, for example chloride, bromide or iodide, or is a methosulfate anion. The alkyl groups recited in $R_2$ and $R_3$ may be straight-chained or branched, but are preferably substantially linear.

Particularly useful quaternary germicides include compositions which include a single quaternary compound, as well as mixtures of two or more different quaternary compounds. Such useful quaternary compounds are available under the BARDAC®, BARQUAT®, HYAMINE®, LONZABAC® and ONYXIDE® trademarks, which are more fully described in, for example, McCutcheon's Functional Materials (Vol. 2), North American Edition, 1998.

The foaming antagonist is present in an amount of from about 0.5 wt-% to about 20 wt-%, preferably from about 1 wt-% to about 15 wt-% and more preferably from about 2 wt-% to about 12 wt-%.

pH Adjuster

The composition of the invention may include a suitable alkali to adjust the final pH of the composition to a pH of from 7.0 to 12.5, preferably from 9.0 to 11.5. Suitable pH adjusters include potassium hydroxide, sodium hydroxide citric acid, and ammonium hydroxide, and they are suitably included in an amount of from 0.05 to 5 wt % in order to adjust the pH to the desired level.

Carrier

The composition of the invention includes a suitable carrier which is preferably an aqueous carrier, most preferably water, suitably deionised water. The carrier is present in an amount of from 0 to 99 wt-% preferably from about 1 to 80 wt-% and more preferably from about 10 wt-% to about 60 wt-%, to make up the remainder of the composition to a total of 100 wt %, in addition to the components described above to form the concentrate composition which may be further diluted as described herein to form a use solution.

Chelating Agent

The composition is generally a concentrate or a ready to use composition that includes a chelating agent. In general, a chelating agent is a molecule capable of coordinating (i.e., binding) the metal ions commonly found in water sources to prevent the metal ions from interfering with the action of the other ingredients. Examples of chelating agents include phosphonic acid and phosphonates, phosphates, aminocarboxylates and their derivatives, pyrophosphates, ethylenediamine and ethylenetriamine derivatives, hydroxyacids, and mono-, di-, and tri-carboxylates and their corresponding acids. In certain embodiments the composition is phosphate free. Preferred chelating agents form calcium-chelating agent complexes with a stability constant (expressed in logarithmic form) of about 5.5 or greater. The calcium-chelating agent stability constant (K) is the measure of the stability of a calcium-chelating agent complex (CaL) formed by the reaction of a calcium ion (Ca) with a chelating agent (L) in aqueous solution.

$$Ca+L \rightleftharpoons CaL$$

The stability constant is expressed as:

$$K = \frac{[CaL]}{[Ca][L]}$$

Where:

K=stability constant for the calcium-chelating agent complex

[CaL]=concentration (mol/L) of the calcium-chelating agent complex

[Ca]=concentration (mol/L) of calcium ions

[L]=concentration (mol/L) of the chelating agent

Preferred chelating agents are selected from the group comprising ethylenediaminetetraacetic acid (EDTA); diethylenetriaminepentacetic acid (DTPA); methylglycine-N,N-diacetic acid (MGDA); glutamic acid-N,N-diacetic acid (GLDA); Aspartic acid-N,N-diacetic acid (ASDA) and alkali, alkali earth metal, transition metal and/or ammonium salts thereof. When present, the chelating agent is present in an amount of from about 5 wt-% to about 40 wt-%, from about 10 wt-% to about 35 wt-% and more preferably in an amount of form about 15 wt-% to about 30 wt-%.

Other Components

In other embodiments, additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in the particular use as a foaming bathroom cleaner and/or foaming hard surface cleaner. Some particular examples of functional materials are discussed in more detail below, although the particular materials discussed are given by way of example only, and that a broad variety of other functional ingredients may be used.

In some embodiments the compositions may include preservatives and/or fragrances and/or dyes. In still further embodiments the compositions may include a biocide, antimicrobial, solvents, additional surfactants, dispersants, stabilizing agents, rheology modifiers, carriers, buffers, and the like.

Additional Surfactants

According to the invention the cleaning compositions may include further surfactants.

Particularly suitable surfactants for use in the bathroom and other hard surface cleaning compositions of the invention include, for example zwitterionic surfactants. In more preferred aspects, a betaine surfactant, such as cocoamido propyl betaine is preferred. As set forth in this description of the invention, addition classes of surfactants may be employed, and are described below.

Nonionic Surfactants

Additional nonionic surfactants may be used which are not high foaming as described above. Useful nonionic surfactants are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties. Useful nonionic surfactants include:

Condensation products of one mole of a saturated or unsaturated, straight or branched chain alcohol having from about 6 to about 24 carbon atoms with from about 3 to about 50 moles of ethylene oxide. The alcohol moiety can consist of mixtures of alcohols in the above delineated carbon range or it can consist of an alcohol having a specific number of carbon atoms within this range. Examples of like commercial surfactant are available under the trade names Neodol™ manufactured by Shell Chemical Co. and Alfonic™ manufactured by Vista Chemical Co.

Condensation products of one mole of saturated or unsaturated, straight or branched chain carboxylic acid having from about 8 to about 18 carbon atoms with from about 6 to about 50 moles of ethylene oxide. The acid moiety can consist of mixtures of acids in the above defined carbon atoms range or it can consist of an acid having a specific number of carbon atoms within the range. Examples of commercial compounds of this chemistry are available on the market under the trade names Nopalcol™ manufactured by Henkel Corporation and Lipopeg™ manufactured by Lipo Chemicals, Inc. In addition to ethoxylated carboxylic acids, commonly called polyethylene glycol esters, other alkanoic acid esters formed by reaction with glycerides, glycerin, and polyhydric (saccharide or sorbitan/sorbitol) alcohols have application in this invention for specialized embodiments, particularly indirect food additive applications. All of these ester moieties have one or more reactive hydrogen sites on their molecule which can undergo further acylation or ethylene oxide (alkoxide) addition to control the hydrophilicity of these substances. Care must be exercised when adding these fatty ester or acylated carbohydrates to compositions of the present invention containing amylase and/or lipase enzymes because of potential incompatibility.

Examples of nonionic low foaming surfactants include:

Nonionic compounds which are modified, essentially reversed, by adding ethylene oxide to ethylene glycol to provide a hydrophile of designated molecular weight; and, then adding propylene oxide to obtain hydrophobic blocks on the outside (ends) of the molecule. The hydrophobic portion of the molecule weighs from about 1,000 to about 3,100 with the central hydrophile including 10% by weight to about 80% by weight of the final molecule. These reverse Pluronics™ are manufactured by BASF Corporation under the trade name Pluronic™ R surfactants. Likewise, the Tetronic™ R surfactants are produced by BASF Corporation by the sequential addition of ethylene oxide and propylene oxide to ethylenediamine. The hydrophobic portion of the molecule weighs from about 2,100 to about 6,700 with the central hydrophile including 10% by weight to 80% by weight of the final molecule.

Nonionic compounds which are modified by "capping" or "end blocking" the terminal hydroxy group or groups (of multi-functional moieties) to reduce foaming by reaction with a small hydrophobic molecule such as propylene oxide, butylene oxide, benzyl chloride; and, short chain fatty acids, alcohols or alkyl halides containing from 1 to about 5 carbon atoms; and mixtures thereof. Also included are reactants such as thionyl chloride which convert terminal hydroxy groups to a chloride group. Such modifications to the terminal hydroxy group may lead to all-block, block-heteric, heteric-block or all-heteric nonionics.

Additional examples of effective low foaming nonionics include:

The alkylphenoxypolyethoxyalkanols of U.S. Pat. No. 2,903,486 issued Sep. 8, 1959 to Brown et al. and represented by the formula

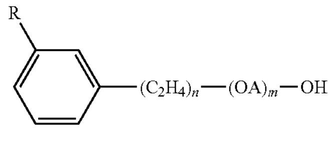

in which R is an alkyl group of 8 to 9 carbon atoms, A is an alkylene chain of 3 to 4 carbon atoms, n is an integer of 7 to 16, and m is an integer of 1 to 10.

The polyalkylene glycol condensates of U.S. Pat. No. 3,048,548 issued Aug. 7, 1962 to Martin et al. having alternating hydrophilic oxyethylene chains and hydrophobic oxypropylene chains where the weight of the terminal hydrophobic chains, the weight of the middle hydrophobic unit and the weight of the linking hydrophilic units each represent about one-third of the condensate.

The defoaming nonionic surfactants disclosed in U.S. Pat. No. 3,382,178 issued May 7, 1968 to Lissant et al. having the general formula $Z[(OR)_nOH]_z$ wherein Z is alkoxylatable material, R is a radical derived from an alkaline oxide which can be ethylene and propylene and n is an integer from, for example, 10 to 2,000 or more and z is an integer determined by the number of reactive oxyalkylatable groups.

The conjugated polyoxyalkylene compounds described in U.S. Pat. No. 2,677,700, issued May 4, 1954 to Jackson et al. corresponding to the formula $Y(C_3H_6O)_n\ (C_2H_4O)_mH$ wherein Y is the residue of organic compound having from about 1 to 6 carbon atoms and one reactive hydrogen atom, n has an average value of at least about 6.4, as determined by hydroxyl number and m has a value such that the oxyethylene portion constitutes about 10% to about 90% by weight of the molecule.

The conjugated polyoxyalkylene compounds described in U.S. Pat. No. 2,674,619, issued Apr. 6, 1954 to Lundsted et al. having the formula $Y[(C_3H_6O_n\ (C_2H_4O)_mH]_x$ wherein Y is the residue of an organic compound having from about 2 to 6 carbon atoms and containing x reactive hydrogen atoms in which x has a value of at least about 2, n has a value such that the molecular weight of the polyoxypropylene hydrophobic base is at least about 900 and m has value such that the oxyethylene content of the molecule is from about 10% to about 90% by weight. Compounds falling within the scope of the definition for Y include, for example, propylene glycol, glycerine, pentaerythritol, trimethylolpropane, ethylenediamine and the like. The oxypropylene chains optionally, but advantageously, contain small amounts of ethylene oxide and the oxyethylene chains also optionally, but advantageously, contain small amounts of propylene oxide.

Additional conjugated polyoxyalkylene surface-active agents which are advantageously used in the compositions of this invention correspond to the formula: $P[(C_3H_6O)_n\ (C_2H_4O)_mH]_x$ wherein P is the residue of an organic compound having from about 8 to 18 carbon atoms and containing x reactive hydrogen atoms in which x has a value of 1 or 2, n has a value such that the molecular weight of the polyoxyethylene portion is at least about 44 and m has a value such that the oxypropylene content of the molecule is from about 10% to about 90% by weight. In either case the oxypropylene chains may contain optionally, but advantageously, small amounts of ethylene oxide and the oxyethylene chains may contain also optionally, but advantageously, small amounts of propylene oxide.

Polyhydroxy fatty acid amide surfactants suitable for use in the present compositions include those having the structural formula $R_2CON_{R1}Z$ in which: R1 is H, $C_1$-$C_4$ hydrocarbyl, 2-hydroxy ethyl, 2-hydroxy propyl, ethoxy, propoxy group, or a mixture thereof; $R_2$ is a $C_5$-$C_{31}$ hydrocarbyl, which can be straight-chain; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z can be derived from a reducing sugar in a reductive amination reaction; such as a glyceryl moiety.

The alkyl ethoxylate condensation products of aliphatic alcohols with from about 0 to about 25 moles of ethylene oxide are suitable for use in the present compositions. The alkyl chain of the aliphatic alcohol can either be straight or branched, primary or secondary, and generally contains from 6 to 22 carbon atoms.

Suitable nonionic alkylpolysaccharide surfactants, particularly for use in the present compositions include those disclosed in U.S. Pat. No. 4,565,647, Llenado, issued Jan. 21, 1986. These surfactants include a hydrophobic group containing from about 6 to about 30 carbon atoms and a polysaccharide, e.g., a polyglycoside, hydrophilic group containing from about 1.3 to about 10 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Fatty acid amide surfactants suitable for use the present compositions include those having the formula: $R_6CON(R_7)_2$ in which $R_6$ is an alkyl group containing from 7 to 21 carbon atoms and each $R_7$ is independently hydrogen, $C_1$-$C_4$ alkyl, $C_1$-$C_4$ hydroxyalkyl, or $—(C_2H_4O)_xH$, where x is in the range of from 1 to 3.

A useful class of non-ionic surfactants includes the class defined as alkoxylated amines or, most particularly, alcohol alkoxylated/aminated/alkoxylated surfactants. These non-ionic surfactants may be at least in part represented by the general formulae: $R^{20}—(PO)_SN\text{-}(EO)_tH$, $R^{20}—(PO)_SN\text{-}(EO)_tH(EO)_tH$, and $R^{20}—N(EO)_tH$; in which $R^{20}$ is an alkyl, alkenyl or other aliphatic group, or an alkyl-aryl group of from 8 to 20, preferably 12 to 14 carbon atoms, EO is oxyethylene, PO is oxypropylene, s is 1 to 20, preferably 2-5, t is 1-10, preferably 2-5, and u is 1-10, preferably 2-5. Other variations on the scope of these compounds may be represented by the alternative formula: $R^{20}—(PO)_V—N[(EO)_wH][(EO)_zH]$ in which $R^{20}$ is as defined above, v is 1 to 20 (e.g., 1, 2, 3, or 4 (preferably 2)), and w and z are independently 1-10, preferably 2-5. These compounds are represented commercially by a line of products sold by Huntsman Chemicals as nonionic surfactants. A preferred chemical of this class includes Surfonic™ PEA 25 Amine Alkoxylate. Preferred nonionic surfactants for the compositions of the invention include alcohol alkoxylates, EO/PO block copolymers, alkylphenol alkoxylates, and the like.

The treatise *Nonionic Surfactants*, edited by Schick, M. J., Vol. 1 of the Surfactant Science Series, Marcel Dekker, Inc., New York, 1983 is an excellent reference on the wide variety of nonionic compounds generally employed in the practice of the present invention. A typical listing of nonionic classes, and species of these surfactants, is given in U.S. Pat. No. 3,929,678 issued to Laughlin and Heuring on Dec. 30, 1975. Further examples are given in "Surface Active Agents and detergents" (Vol. I and II by Schwartz, Perry and Berch). These references are herein incorporated in their entirety.

Anionic Surfactants

Also useful in the present invention are surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility. As those skilled in the art understand, anionics are excellent detersive surfactants and are therefore favored additions to heavy duty detergent compositions.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

$$R—O—(CH_2CH_2O)_n(CH_2)_m—CO_2X \quad (3)$$

in which R is a $C_8$ to $C_{22}$ alkyl group or

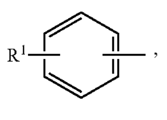

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

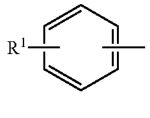

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Cationic Surfactants

Surface active substances are classified as cationic if the charge on the hydrotrope portion of the molecule is positive. Surfactants in which the hydrotrope carries no charge unless the pH is lowered close to neutrality or lower, but which are then cationic (e.g. alkyl amines), are also included in this group. In theory, cationic surfactants may be synthesized from any combination of elements containing an "onium" structure RnX+Y— and could include compounds other than nitrogen (ammonium) such as phosphorus (phosphonium) and sulfur (sulfonium). In practice, the cationic surfactant field is dominated by nitrogen containing compounds, probably because synthetic routes to nitrogenous cationics are simple and straightforward and give high yields of product, which can make them less expensive.

Cationic surfactants preferably include, more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amine oxides, amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution.

The simplest cationic amines, amine salts and quaternary ammonium compounds can be schematically drawn thus:

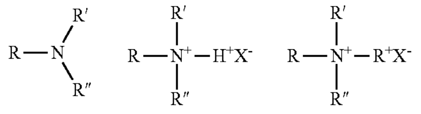

in which, R represents a long alkyl chain, R', R", and R'" may be either long alkyl chains or smaller alkyl or aryl groups or hydrogen and X represents an anion. The amine salts and quaternary ammonium compounds are preferred for practical use in this invention due to their high degree of water solubility.

The majority of large volume commercial cationic surfactants can be subdivided into four major classes and additional sub-groups known to those or skill in the art and described in "Surfactant Encyclopedia", *Cosmetics & Toiletries*, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Cationic surfactants useful in the compositions of the present invention include those having the formula $R^1_m R^2_x Y_L Z$ wherein each $R^1$ is an organic group containing a straight or branched alkyl or alkenyl group optionally substituted with up to three phenyl or hydroxy groups and optionally interrupted by up to four of the following structures:

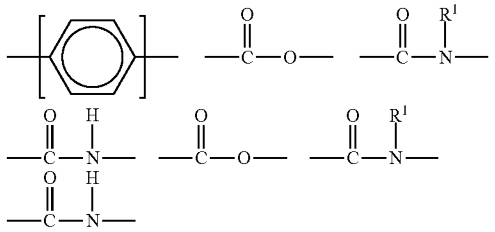

or an isomer or mixture of these structures, and which contains from about 8 to 22 carbon atoms. The $R^1$ groups can additionally contain up to 12 ethoxy groups. m is a number from 1 to 3. Preferably, no more than one $R^1$ group in a molecule has 16 or more carbon atoms when m is 2 or more than 12 carbon atoms when m is 3. Each $R^2$ is an alkyl or hydroxyalkyl group containing from 1 to 4 carbon atoms or a benzyl group with no more than one $R^2$ in a molecule being benzyl, and x is a number from 0 to 11, preferably from 0 to 6. The remainder of any carbon atom positions on the Y group are filled by hydrogens. Y is can be a group including, but not limited to:

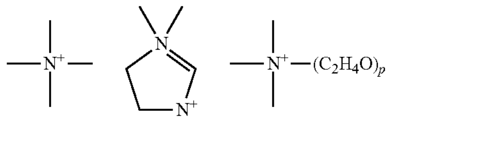

p ~ about 1 to 12

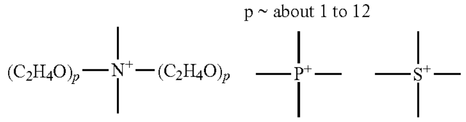

p = about 1 to 12

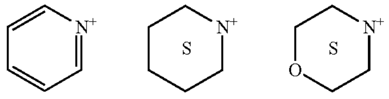

or a mixture thereof. Preferably, L is 1 or 2, with the Y groups being separated by a moiety selected from $R^1$ and $R^2$ analogs (preferably alkylene or alkenylene) having from 1 to about 22 carbon atoms and two free carbon single bonds when L is 2. Z is a water soluble anion, such as a halide, sulfate, methylsulfate, hydroxide, or nitrate anion, particularly preferred being chloride, bromide, iodide, sulfate or methyl sulfate anions, in a number to give electrical neutrality of the cationic component.

Amphoteric Surfactants

Additional amphoteric surfactants other than those listed above may be used in the compositions of the invention. Amphoteric surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

A typical listing of amphoteric classes, and species of these surfactants, is given in U.S. Pat. No. 3,929,678 issued to Laughlin and Heuring on Dec. 30, 1975. Further examples are given in “Surface Active Agents and Detergents” (Vol. I and II by Schwartz, Perry and Berch). Each of these references are herein incorporated by reference in their entirety.

Zwitterionic Surfactants

According to the invention the cleaning compositions may include a zwitterionic surfactant, such as a betaine surfactant. Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong “inner-salt” attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate.

Betaine and sultaine surfactants are exemplary zwitterionic surfactants for use herein. A general formula for these compounds is:

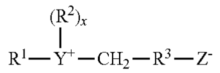

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

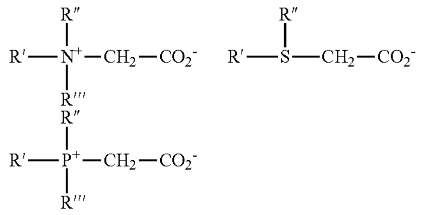

These surfactant betaines typically do not exhibit strong cationic or anionic characters at pH extremes nor do they show reduced water solubility in their isoelectric range. Unlike “external” quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2N^+R^2SO^{3-}$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in “Surface Active Agents and Detergents” (Vol. I and II by Schwartz, Perry and Berch). Each of these references is herein incorporated by reference in their entirety.

Dyes or Odorants

Various dyes, odorants including perfumes, and other aesthetic enhancing agents may also be included in the compositions. Dyes may be included to alter the appearance of the composition, as for example, Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keyston Analine and Chemical), Metanil Yellow (Keystone Analine and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (Ciba-Geigy), Liquitint Pink AL and the like. Fragrances or perfumes that may be included in the compositions include, for example, terpenoids such as citronellol, aldehydes such as amyl cinnamaldehyde, a jasmine such as ClS-jasmine orjasmal, vanillin, and the like.

In an aspect, the compositions include from about 0 wt-%-20 wt-% dyes and/or odorants, from about 0.001 wt-%-10 wt-% dyes and/or odorants, from about 0.01 wt-%-5 wt-% dyes and/or odorants, preferably from about 0.01 wt-%-2 wt-% dyes and/or odorants. In addition, without being limited according to the invention, all ranges recited are inclusive of the numbers defining the range and include each integer within the defined range.

Preservatives

In some embodiments, the compositions of the present invention include a preservative. In an aspect, preservatives which do not include a disinfectant component are particularly suited for use in the cleaning compositions. Various preservative compositions known in the art may be employed. An example of a suitable preservative includes those commercially-available under the tradename Kathon® CG/ICP (Rohm & Haas, Philadelphia Pa.).

In an aspect, the compositions include from about 0 wt-%-20 wt-% preservative, from about 0.001 wt-%-10 wt-% preservative, from about 0.01 wt-%-5 wt-% preservative, preferably from about 0.01 wt-%-2 wt-% preservative. In addition, without being limited according to the invention, all ranges recited are inclusive of the numbers defining the range and include each integer within the defined range.

Bleaching Agents

Bleaching agents that may be used in a cleaning composition for lightening or whitening a substrate, include bleaching compounds capable of liberating an active halogen species, such as —Cl, —Br, —OCl and/or —Obr, under conditions typically encountered during the cleansing process. Suitable bleaching agents for use in the present cleaning compositions include, for example, chlorine-containing compounds such as a chlorine, hypochlorite, chloramine, and the like. Preferred halogen-releasing compounds include the alkali metal dichloroisocyanurates, chlorinated trisodium phosphate, the alkali metal hypochlorides, monochloramine and dichloramine, and the like. Encapsulated chlorine sources may also be used to enhance the stability of the chlorine source in the composition (see, for example, U.S. Pat. No. 4,618,914, the disclosure of which is incorporated by reference herein). A bleaching agent may also be a peroxygen or active oxygen source such as hydrogen peroxide, perborates, sodium carbonate peroxyhydrate, phosphate peroxyhydrates, potassium permonosulfate, and sodium perborate mono and tetrahydrate, with and without activators such as tetraacetylethylene diamine, and the like. A cleaning composition may include a minor but effective amount of a bleaching agent, preferably about 0.1 to 10 wt-%, preferably about 1 to 6 wt-%.

Anti Redeposition Agents

A cleaning composition may also include an anti-redeposition agent capable of facilitating sustained suspension of soils in a cleaning solution and preventing removed soils from being redeposited onto the substrate being cleaned. Examples of suitable anti-redeposition agents include fatty acid amides, fluorocarbon surfactants, complex phosphate esters, styrene maleic anhydride copolymers, and cellulosic derivatives such as hydroxyethyl cellulose, hydroxypropyl cellulose, carboxymethyl cellulose, and the like. A cleaning composition may include about 0.5 to 10 wt-%, preferably about 1 to 5 wt-%, of an anti-redeposition agent.

Embodiments

The composition of the invention is suitably packaged in a foam-forming pump dispenser to provide the cleaning system of the invention. Such manual foam-forming dispensers are well known in the art, for example those disclosed in EP 0613728. These dispensers generally comprise a pump assembly which can be mounted on or in an opening of a reservoir for holding the liquid to be dispensed in the form of a foam. The pump assembly comprises a liquid pump for pumping the liquid from the reservoir and an air pump to mix air with the liquid in order to form a foam or mousse. The foam is then dispensed through a dispensing channel out of a dispensing opening. In the dispersing channel, one or more meshes or sieves may be arranged to ensure a homogenous foam. Suitable pump dispensers will have a capacity of from 50 ml to 600 ml, preferably from 100 ml to 200 ml, more preferably 150 ml.

A suitable pump dispenser is the G3 Up and Down Stroke Dispenser from Rexam.

The composition of the present invention is a foaming cleaning composition. The composition may be dispensed in the form of a mousse or aerated foam from the system of the invention. In the present context, the terms mousse, foaming composition and aerated foam are interchangeable and are intended to mean a composition that remains in foam form after it is dispensed until it is mechanically compressed or is evaporated.

In use, the foaming composition is dispensed from the foam- or mousse-forming pump dispenser. Suitably, an amount of up to 200 ml, suitably from 150 to 180 ml, of the composition may be applied using the dispenser. The composition of the invention may be applied in one single pump application or in the form of a number of individual pumped amounts dispensed from the pump dispenser, each of suitably approximately 20 to 40 ml each, preferably about 30 ml each. A number of the individual amounts may be applied, say up to 10, preferably up to 8, more preferably up to 6 separate applications inside the cleaning. The foaming composition may be applied to the walls, ceiling, floor or inner door surface of the cleaning oven, but will preferably be applied to the floor of the cleaning oven or to a removable internal plate of the oven, if present.

The compositions of the present invention can be used to remove stains from any conventional bathroom surfaces including but not limited to, toilets, shower stalls, racks, curtains, shower doors, bathing appliances, shower bars, bathtubs, bidets, sinks, etc., as well as countertops, walls, floors, etc. Additional hard surfaces which may be cleaned using the compositions of the invention, include for example, counter tops, tile, floors, walls, windows, fixtures, kitchen furniture, appliances, and the like.

The various hard surfaces suitable for cleaning according to the invention include for example, glass; metals; plastics e.g. polyester, vinyl; fiberglass, Formica®, Corian®; refractory materials such as: glazed and unglazed tile, brick, porcelain, ceramics as well as stone including marble, granite, and other stones surfaces; and other hard surfaces known to the industry.

In conventional, industrial and/or commercial bathroom and/or hard surface applications of use, the methods of removing soils from a soiled surface may be employed using concentrated formulation. In such aspects of use employing a concentrated formulation, dilution steps may be initially employed to provide a water source to the concentrated formulation suitable for generating a use solution or use composition. In some aspects, the concentrated cleaning composition may be diluted at a dilution factor between approximately 1 to about 16 ounces liquid concentrate per gallon of water diluent, preferably from about 1 to about 12 ounces liquid concentrate per gallon of water diluent, and more preferably from about 8 to about ounces liquid concentrate per gallon of water diluent. In some aspects, the dilution step occurs at or near a point of use, and may include for example use of a water source that is provided using an aspirator or other dilution mechanism known to the art. In other aspects, when the cleaning composition is employed in a diluted (or a use solution or composition) formulation no further dilution is required by a user.

A particularly well suited method for applying or contacting the cleaning composition to a soiled surface is through the use of a manually operated spray-dispensing container. The spray-dispensing container preferably includes a spray nozzle, a dip tube and associated pump dispensing parts, providing convenient application to soiled bathroom and/or other hard surfaces.

In an embodiment of the methods of the invention, the cleaning composition contacts the surface in need of cleaning. This step may include a contact time from a few seconds to a few minutes, such as from about 30 seconds to about 30 minutes. In such application or contacting step, the user applies an effective amount of the cleaning composition using the spray-dispensing container (or other application means) and within a few seconds to a few minutes thereafter, wipes off the treated area with a rag, towel, sponge or other item (e.g. a disposable paper towel or sponge). In some embodiments involving heavy soil deposits, the cleaning composition may be left on the soiled surface until it has effectively loosened the soil deposits, after which it may be wiped off, rinsed off, or otherwise removed. For particularly heavy deposits of such undesired stains, multiple applications may also be used.

The contacting step may optionally include the use of additional cleaning components, such as for example surfactants, bleaching agents and/or antimicrobial agents. The contacting step may be conducted at a broad range of temperatures, which are not intended to limit the scope of the invention.

In an aspect of the methods of the invention, the cleaning composition may be applied using mechanical force during the contacting step. For example, for removing certain soils from the hard surface additional force may need to be applied, e.g. applying a water source and/or mechanical force to assist in removing soils.

In an additional optional embodiment of the methods of the invention, the cleaning composition may be rinsed from a surface after the initial contacting step. In yet other embodiments the cleaning composition is wiped off the soiled surface, effectively removing the soils and any remaining cleaning composition. In further aspects, there is no need for a rinse step.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are indicative of the level of ordinary skill in the art to which this invention pertains, and are hereby incorporated by reference. The invention is further illustrated by the following examples, which should not be construed as further limiting.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Formulations were made and tested per the table below.

| | FSC 35K | FSC 35K1 | FSC 35K2 |
|---|---|---|---|
| Water | 51.58 | 47.58 | 59.58 |
| chelant | 25.00 | 25.00 | 25.00 |
| Amine oxide surfactant | 7.00 | 7.00 | 7.00 |
| solvent | 5.00 | 5.00 | 5.00 |
| Cocamidopropyl Phosphatidyl PG-Dimonium Chloride (solvent) | 0.00 | 4.00 | 0.00 |
| Citric Acid 50% White | 2.00 | 2.00 | 2.00 |
| quaternary ammonium compound | 8.00 | 8.00 | 0.00 |
| fragrance | 0.40 | 0.40 | 0.40 |
| coloring | 0.020 | 0.020 | 0.020 |
| | 100.000 | 100.000 | 100.000 |

| | Foam Dwell Time in Minutes | | | | |
|---|---|---|---|---|---|
| | Rep 1 | Rep 2 | Rep 3 | Rep 4 | Average |
| FSC 35K | 2.5 | 3.5 | 2.0 | 2.5 | 2.6 |
| FSC 35K1 | 7.0 | 8.0 | 7.5 | 8.0 | 7.6 |
| FSC 35K2 | 6.5 | 7.0 | 6.0 | 6.0 | 6.4 |

FSC 35K2 shows a typical foaming bathroom cleaning composition with no cocamidopropyl synergist and no foaming antagonist (cationic active) in comparison with the dwell time of the compositions of the invention. FSC 35K1 and FSC 35K2 are compositions which include the foam synergist and foam antagonist according to the invention. From the results one can see that a shorter dwell time occurs with the presence of the antagonist and no synergist and a longer dwell time occurs with the presence of both.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A foaming cleaning composition comprising:

an amine oxide as a foaming surfactant;

from 4 wt-% to about 15 wt-% of cocamidopropyl phosphatidyl PG-dimonium chloride as a foaming synergist with said foaming surfactant; and from 8 wt-% to about 20 wt-% of dodecyl dimethyl ammonium chloride as a foaming antagonist, with the remainder being water or other functional components, said composition having a pH from 7.0 to 12.5, wherein the composition is free of cationic nitrogen containing polymers.

2. The cleaning composition of claim 1, wherein said amine oxide is one or more of the following: lauryl dimethyl amine oxide, cocamine oxide, and/or octyl dimethyl amine oxide.

3. The cleaning composition of claim 1, wherein said composition further comprises one or more of the following: diethylene glycol butyl ether, diethylene glycol ethyl ether, propylene glycol, and/or hexylene glycol.

4. A foaming cleaning composition comprising:

a) from about 0.5 wt-% to about 20 wt-% of an amine oxide as a foaming surfactant;

b) from 4 wt-% to about 15 wt-% of cocamidopropyl phoshatidyl PG-dimonium chloride as a foaming synergist; and c) from 8 wt-% to about 20 wt-% of dodecyl dimethyl ammonium chloride as a foaming antagonist, with the remainder being water, or other functional components, said composition having a pH of from 7.0 to 12.5, wherein the composition is free of cationic nitrogen containing polymers.

5. The cleaning composition of claim 4, wherein said amine oxide is lauryl dimethyl amine oxide, cocamine oxide, and/or octyl dimethyl amine oxide.

6. The cleaning composition of claim 4, wherein said composition further comprises one or more of the following: diethylene glycol butyl ether, diethylene glycol ethyl ether, propylene glycol, and/or hexylene glycol.

7. A method of cleaning a hard surface to remove soil and/or debris comprising:

applying a foaming cleaning composition comprising:

an amine oxide as a foaming surfactant; from 4 wt-% to about 15 wt-% of cocamidopropyl phosphatidyl PG-dimonium chloride as a foaming synergist with said foaming surfactant; and from 8 wt-% to about 20 wt-% of a dodecyl dimethyl ammonium chloride as a foaming antagonist, with the remainder being water or other functional components, said composition having a pH from 7.0 to 12.5, wherein the composition is free of cationic nitrogen containing polymers, to the surface;

allowing the foam to dissipate, and thereafter rinsing said surface so that said composition and said soil and/or debris are removed.

8. The method of claim 7 wherein said foam dissipation takes about 2 to 3 minutes.

9. The method of claim 7 wherein said foam dissipation results in an audible cracking sound.

10. The method of claim 7 wherein said hard surface is a bathroom surface.

11. The method of claim 7 wherein said hard surface is one of the following: stainless steel, aluminum, copper, vinyl, plastic, metal, glass, natural rubber, synthetic rubber, formica, wood, mild steel, melamine, brass, ceramic, or stone.

12. The method of claim 7 wherein said surface is a nonhorizontal surface.

13. The method of claim 12 wherein said nonhorizontal surface is on a toilet, glass, mirror, shower, transportation vehicle, or wall.

* * * * *